US005644041A

United States Patent [19]
Johansson

[11] Patent Number: 5,644,041
[45] Date of Patent: Jul. 1, 1997

[54] ALKYL GLYCOSIDE ITS USE FOR CLEANING PURPOSES, AND CLEANING COMPOSITION

[75] Inventor: Ingegärd Johansson, Göteborg, Sweden

[73] Assignee: Akzo Nobel nv, Arhem, Netherlands

[21] Appl. No.: 507,439

[22] PCT Filed: Mar. 10, 1994

[86] PCT No.: PCT/SE94/00198

§ 371 Date: Oct. 18, 1995

§ 102(e) Date: Oct. 18, 1995

[87] PCT Pub. No.: WO94/21769

PCT Pub. Date: Sep. 29, 1994

[30] Foreign Application Priority Data

Mar. 23, 1993 [SE] Sweden .................................. 9300954

[51] Int. Cl.$^6$ ............................ C07G 3/00; C07H 15/04; C11D 1/00

[52] U.S. Cl. ........................ 536/4.1; 536/18.5; 536/18.6; 536/120; 510/245; 510/470

[58] Field of Search ................................ 536/18.5, 18.6, 536/4.1, 120; 514/25; 252/174.17

[56] References Cited

U.S. PATENT DOCUMENTS

| | | | |
|---|---|---|---|
| 3,772,269 | 11/1973 | Lew | 260/210 R |
| 3,839,318 | 10/1974 | Manfield | 260/210 R |
| 4,483,779 | 11/1984 | Llenado et al. | 252/135 |
| 4,847,368 | 7/1989 | Lueders et al. | 536/18.6 |
| 4,898,934 | 2/1990 | Lueders et al. | 536/18.6 |
| 4,990,605 | 2/1991 | Lueders | 536/18.5 |

FOREIGN PATENT DOCUMENTS

| | | | |
|---|---|---|---|
| 0 306 650 | 3/1989 | European Pat. Off. | C07H 15/04 |
| 0 306 652 | 3/1989 | European Pat. Off. | C07H 15/04 |
| 0 306 651 | 3/1989 | European Pat. Off. | C07H 15/04 |
| 20 36 472 | 2/1971 | Germany | C07H 15/04 |
| 1072655 | 6/1967 | United Kingdom . | |
| 88/09369 | 1/1988 | WIPO . | |

OTHER PUBLICATIONS

U.S. Statutory Invention Registration, Reg. No. H171, Published Dec. 2, 1986.

U.S. Statutory Invention Registration, Reg. No. H468, Published May 3, 1988.

Justus Leibig's Annalen Der Chemie (1985), (8) , pp. 1513–1536 Paulsen et al.

*Primary Examiner*—John Kight
*Assistant Examiner*—Everett White
*Attorney, Agent, or Firm*—Ralph J. Mancini; Louis A. Morris

[57] ABSTRACT

The present invention generally relates to an alkyl glycoside of the formula (I): $RCH_2O(G)_x$ H, wherein R is an alkyl group having a total of 8–12 carbon atoms and containing 2–4 groups of the formula —$CH(CH_3)$— in its carbon chain; G is a monosaccharide residue; and x is 1–4. The invention also relates to the use of the alkyl glycoside as a surfactant in the cleaning of hard surfaces. A composition containing an alkyl glycoside of formula (I), a complexing agent and a solubilizer is also disclosed.

12 Claims, No Drawings

ALKYL GLYCOSIDE ITS USE FOR CLEANING PURPOSES, AND CLEANING COMPOSITION

This application is a 371 of PCT/SE94/00198.

This invention relates to an alkyl glycoside in which the alkyl group is methyl-branched, as well as the use of the alkyl glycoside as a surfactant in the cleaning of hard surfaces. The invention also concerns a cleaning composition in which the alkyl glycoside is combined with a solubiliser and preferably also with a complexing agent.

In recent years, attention has focused on alkyl glycosides, since these have proved to be more easily biodegradable than other non-ionic surfactants, such as ethylene oxide adducts of fatty alcohols. U.S. Pat. No. 3,839,318 thus describes the production of alkyl glycosides and alkyl oligosaccharides, such as n-octyl glycoside, n-hexyl glycoside, n-decyl glycoside, n-dodecyl glycoside, isodecyl glycoside, isoundecyl glycoside, isotridecyl glucoside and the corresponding oligosaccharides. The United States Stationary Invention Registration H171 states that alkyl glycosides of formulae R(OG) and $R(OG)_x$ are excellent surfactants. In these formulae, R is an alkyl or alkenyl group which is branched at the second carbon atom or at a higher carbon atom, the branch being selected from the group methyl, ethyl, isopropyl, n-propyl, butyl, pentyl, hexyl and mixtures thereof, provided that R contains from about 7 to about 30 carbon atoms; G is a saccharide group selected from the group glucose, fructose, mannose, galactose, talose, allose, altrose, idose, arabinose, xylose, lyxose, ribose and mixtures thereof; and x is 2 or more. Example 1 contains a description of the production of two product mixtures substantially made up of 2-ethylhexyl glycoside and isooctyl glycoside, respectively.

DE 20 36 472, EP 306 650, EP 306 651 and EP 306 652, inter alia, also describe alkyl glycosides.

Even though alkyl glycosides generally are easily biodegradable, they are only used to a limited extent in many ranges of application, such as the cleaning of hard surfaces, since they are too high-foaming and/or have too poor a cleaning power. It is therefore a desideratum to provide non-ionic surfactants which are about as easily biodegradable, but which have a better cleaning effect on hard surfaces and/or are more low-foaming than known alkyl glycosides.

According to the present invention, it has now surprisingly been found that an alkyl glycosides of formula $RCH_2O(G)_xH$ (I)

wherein R is an alkyl group having a total of 8–12 carbon atoms and containing 2–4 groups of formula $—CH(CH_3)—$ in its carbon chain, G is a monosaccharide residue, and x is 1–4, is advantageously used as a surfactant in compositions for cleaning hard surfaces. The alkyl glycosides of formula I shows good cleaning and wetting properties, as well as low foaming compared with other alcohols of approximately the same chain length. In addition, the alkyl glycosides has proved to be easily degradable and have low biotoxicity. Tests have not shown any skin irritations caused by the alkyl glycosides. Preferably, there are 2 or 3 methyl groups. Compounds in which R contains 9 or 10 carbon atoms and x is 1 or 2 are especially preferred, having a good cleaning power and being comparatively easy to produce.

The compounds according to the invention can be produced in conventional manner by reacting an alcohol of formula $RCH_2OH$ (II)

wherein R is as indicated above, with a monosaccharide in the presence of an acid catalyst, the molar ratio of the alcohol to the monosaccharide being 2:1–80:1. The catalyst may be an inorganic or organic acid. The reaction is performed under vacuum at 90°–120° C. for about 1–4 h. Conveniently, the resulting reaction mixture is first filtered and then neutralised with an organic and/or an inorganic base, whereupon excess alcohol is carefully removed e.g. by distillation, if so desired.

The alcohols of formula (I) can be produced in conventional manner by condensing propene, butene or mixtures thereof, whereupon the di-, tri- or tetramers obtained are prolonged with a carbon atom by the oxoprocess. The resulting aldehydes may then easily be converted to the corresponding alcohols. The alcohols obtained form a complex mixture of methyl-branched structures, although some ethyl substituents may be present. The amount of quaternary carbon found in the carbon chain is very small, and alcohols containing quaternary carbon are to be regarded as impurities not encompassed by the invention. Examples of suitable alcohols are Exxal 9, Exxal 10, Exxal 11, Exxal 12 and Exxal 13, all sold by Exxon Chemical. The monosaccharide used as reactant suitably consists of pentose and hexose. Specific examples of monosaccharides used in the production of the inventive glycosides are glucose, mannose, galactose, talose, allose, altrose, idose, arabinose, xylose, ribose and lyxose. Glucose is usually preferred for commercial reasons.

The alkyl glycosides according to the invention are suitable for use in compositions for cleaning hard surfaces, e.g. for degreasing such surfaces or washing up. Excellent results are obtained in the degreasing of lacquered or unlacquered metal surfaces. Apart from the inventive alkyl glycoside, these compositions preferably contain a water-soluble solubiliser and suitably contain a complexing agent.

Examples of solubilisers are alkyl ether polyalkylene glycol, such as monobutyl diethylene glycol; glycols, such as diethylene glycol, dipropylene glycol and propylene glycol; alcohols, such as ethanol, propanol and isopropanol; alkyl glycosides in which the alkyl group has 4–8 carbon atoms; and/or tertiary or quaternary amine alkoxylates in which the alkyl group, which may be straight or branched, saturated or unsaturated, has 8–20 carbon atoms and in which 6–30 mol of alkylene oxide is added per mol of amine. Preferably, 50–100 mol per cent of the added alkylene oxide consists of ethylene oxide, the remainder preferably consisting of propylene oxide or a mixture of propylene oxide and butylene oxide. The different alkylene oxides can be added randomly or in blocks. If the cleaning composition should be exceptionally low-foaming, the alkylene oxide chain conveniently ends with an addition of 1–5 mol of propylene oxide and/or butylene oxide. The ratio of the solubiliser to the inventive alkyl glycoside is usually 1:10–5:1, preferably 1:3–3:1.

The complexing agent may be a conventional inorganic or organic agent, such as an inorganic phosphate or NTA, EDTA, citric acid or a polycarboxylate. The amount added may vary from nothing at all to 300% by weight of the inventive alkyl glycoside. Preferably, the quantitative ratio of the complexing agent to the alkyl glycoside is 1:10–2:1.

The cleaning compositions may further contain other additives, such as pH-adjusting agents, antifoaming agents, enzymes, other surfactants and scents. The compositions are usually aqueous and in the form of emulsions, microemulsions or solutions.

The invention will now be further illustrated by a few Examples.

EXAMPLE 1

An alkyl glycoside was produced by reacting 2.6 mol of an alcohol (Exxal 9) of formula (II), wherein R is a $C_8$ alkyl having a methyl substitution of about 2 (average value), with 0.4 mol of glucose in the presence of 0.015 mol of sulphuric acid as catalyst at 110° C. and 70 mbar. The reaction was interrupted after 105 min. The resulting product mixture was treated by distilling off excess alcohol under vacuum. The yield was 105 g, consisting of 60% of $C_9$-branched alkyl monoglycoside, 15% of $C_9$-branched alkyl diglycoside and a residue of higher oligomers. The glycosides had an average degree of polymerisation (DP) of about 1.5. The structure was determined by gas chromatography, mass spectrometry and NMR.

EXAMPLE 2

An alkyl glycoside was produced by reacting 7.6 mol of an alcohol (Exxal 10) of formula (II), wherein R is a $C_9$ alkyl having a methyl substitution of about 2.2 (average value), with 1.2 mol of glucose in the presence of 0.015 mol of sulphuric acid as catalyst at 90°–111° C. and 100 mbar. The reaction was interrupted after 120 min. The reaction mixture was treated by distilling off excess alcohol under high vacuum. The yield was 278 g, consisting of 60% of monoglycoside, 12% of diglycoside and a residue of higher oligomers. The glycosides had an average DP of 1.6.

EXAMPLE 3

Here, 20 ml of each of the cleaning compositions below, diluted with 10 parts by weight of water per part by weight of the composition, was applied on a vertically arranged iron sheet soiled with mineral oils, soot, salts and clay. After application, the coated surface was rinsed with water without any mechanical treatment.

| | Composition, % by weight | | | | | | |
|---|---|---|---|---|---|---|---|
| Components | 1 | 2 | A | B | C | D | E |
| Glucoside (Example 1) | 5 | | | | | | |
| Glucoside (Example 2) | | 5 | | | | | |
| Glucoside A | | | 5 | | | | |
| Glucoside B | | | | 5 | | | |
| Glucoside C | | | | | 5 | | |
| Glucoside D | | | | | | 5 | |
| Butyldiethylene glycol | | | 11 | 11 | 11 | 11 | 11 |
| Quaternary ethoxylated fatty amine (Berol 555) | 4 | 4 | | | | | |
| NTA | 5 | 5 | 3 | 3 | 3 | 3 | 5 |
| Water | 86 | 86 | 81 | 81 | 81 | 81 | 84 |

Glucoside A = 2-ethylhexyl-O(G)$_x$H
Glucoside B = isooctyl-O(G)$_x$H
Glucoside C = n-dodecyl/n-tetradecyl glucoside (APG-600, Henkel)
Glucoside D = n-decyl glucoside (Lutensol GD-70, BASF) wherein G = glycoside residue and x = 1.5 (average value).

The attained cleaning effect was assessed with respect to the area of the cleaned surface, as well as its actual cleanness, the FIG. 1 indicating no improvement and the FIG. 10 indicating a perfectly clean surface. The following results were obtained.

| Composition | Cleaned surface, $cm^2$ | Cleanness |
|---|---|---|
| 1 | 1112 | 6 |
| 2 | 144 | 8 |
| A | 0 | 1 |
| B | 80 | 4 |
| C | 48 | 6 |
| D | 72 | 6 |
| E | 0 | 1 |

The foaming of the different ready-to-use solutions was measured according to Ross-Miles ASTM D 1173-53. The following results were obtained.

| | Foam height, mm | |
|---|---|---|
| Composition | Instantaneously | After 5 min |
| 1 | 5 | 0 |
| 2 | 8 | 0 |
| A | 7 | 0 |
| B | 20 | 3 |
| C | 67 | 63 |
| D | 46 | 45 |

It is evident from these results that the alkyl glycosides according to the invention show an excellent cleaning power and are clearly superior to alkyl glucosides having a straight carbon chain with 10–14 carbon atoms, while at the same time having an acceptable degree of foaming. The composition containing alkyl glycosides having an alkyl group with 8 carbon atoms showed an unsatisfactory cleaning power.

I claim:

1. An alkyl glycoside of the general formula $RCH_2O(G)_xH$ (I)

wherein R is an alkyl group having a total of 8–12 carbon atoms and containing 2–4 groups of formula $—CH(CH_3)—$ in its carbon chain; G is a monosaccharide residue; and x is 1–4.

2. The alkyl glycoside of claim 1 wherein R is an alkyl group having 9 or 10 carbon atoms.

3. The alkyl glycoside of claim 1 wherein R has a methyl substitution of 2 or 3.

4. The alkyl glycoside of claim 1 wherein G is a glucose residue.

5. The alkyl glycoside of of claim 1 wherein x is 1 or 2.

6. A method for degreasing lacquered or unlacquered metal surfaces which comprises applying to said surfaces, as a surfactant, the alkyl glycoside of claim 1.

7. A cleaning composition which comprises an alkyl glycoside in accordance with claim 1, a water-soluble solubiliser and, optionally, an organic or inorganic complexing agent.

8. The cleaning composition of claim 7, wherein the solubiliser is selected from the group consisting essentially of alkyl ether polyglycols, glycols, alcohols, tertiary alkylamine alkoxylates, quaternary alkylamine alkoxylates, and mixtures thereof.

9. The cleaning composition of claim 7 which comprises the solubiliser in an amount of 1:3–3:1 based on the weight of the alkyl glycoside, and a complexing agent in an amount of 1:10–2:1 based on the weight of the alkyl glycoside.

10. A surfactant for cleaning hard surfaces which comprises an alkyl glycoside of the general formula $RCH_2O(G)_xH$ (I)

wherein R is an alkyl group having a total of 8–12 carbon atoms and containing 2–4 groups of formula $—CH(CH_3)—$ in its carbon chain; G is a monosaccharide residue; and x is 1–4.

11. A process for preparing an alkyl glycoside of formula $RCH_2O(G)_xH$ (I)

wherein R is an alkyl group having a total of 8–12 carbon atoms containing 2–4 groups of formula $—CH(CH_3)—$ in its carbon chain, G is a monosaccharide residue and x is 1–4, which comprises reacting (i) an alcohol of the formula $RCH_2OH$ (II)

wherein R is as indicated above, with (ii) a monosaccharide wherein said reaction is conducted in the presence of an acid catalyst and the ratio of alcohol to monosaccharide is in the range of from 2:1 to 80:1.

12. The process of claim 11 wherein said reaction is conducted at reduced pressure and at a temperature of from 90° C. to 120° C.

* * * * *